(12) United States Patent
Levashov et al.

(10) Patent No.: US 8,075,682 B2
(45) Date of Patent: Dec. 13, 2011

(54) BIOCOMPATIBLE MULTICOMPONENT NANOSTRUCTURED COATINGS FOR MEDICAL APPLICATIONS

(76) Inventors: Evgeny Aleksandrovich Levashov, Moscow (RU); Dmitry Vladimirovich Shtansky, Moscow (RU); Natalya Aleksandrovna Gloushankova, Moscow (RU); Igor Vladimirovich Reshetov, Moscow (RU)

( * ) Notice: Subject to any disclaimer, the term of this patent is extended or adjusted under 35 U.S.C. 154(b) by 873 days.

(21) Appl. No.: 12/085,385

(22) PCT Filed: Oct. 28, 2005

(86) PCT No.: PCT/RU2005/000529
§ 371 (c)(1),
(2), (4) Date: May 22, 2008

(87) PCT Pub. No.: WO2007/004913
PCT Pub. Date: Jan. 11, 2007

(65) Prior Publication Data
US 2009/0050017 A1    Feb. 26, 2009

(30) Foreign Application Priority Data
Jun. 30, 2005  (RU) ............... 2005120397

(51) Int. Cl.
*A61L 27/02* (2006.01)
*A61L 27/10* (2006.01)
*A61K 6/02* (2006.01)

(52) U.S. Cl. ............... 106/286.4; 106/286.2; 106/286.6; 501/96.1

(58) Field of Classification Search ............... 106/286.4, 106/286.2, 296.6; 501/96.1
See application file for complete search history.

(56) References Cited

U.S. PATENT DOCUMENTS

| | | | | |
|---|---|---|---|---|
| 4,212,670 | A | * | 7/1980 | Shveikin et al. ............ 75/233 |
| 4,687,487 | A | * | 8/1987 | Hintermann ............ 623/18.11 |
| 6,057,031 | A | * | 5/2000 | Breme et al. ............ 428/336 |
| 6,177,305 | B1 | * | 1/2001 | Hornback et al. ............ 438/240 |
| 6,344,276 | B1 | | 2/2002 | Lin et al. |
| 2004/0106016 | A1 | * | 6/2004 | Okada et al. ............ 428/698 |

FOREIGN PATENT DOCUMENTS

| | | |
|---|---|---|
| RU | 2 114 580 | 7/1998 |
| RU | 2 115 388 | 7/1998 |
| RU | 2 154 463 | 8/2000 |
| RU | 2 191 842 | 10/2002 |
| SU | 1 803 096 | 3/1993 |

OTHER PUBLICATIONS

International Search Report.
Levashov et al., "Physicochemical and Technological Fundamentals of Self-Propagating High-Temperature Synthesis," Moscow, BIONOM, 1999, entire book. (Spec, p. 4).
Pharr, G. M. et al., "On the generality of the relationship among contact stiffness, contact area, and elastic modulus during indentation," *J. Mater. Res.*, vol. 7, No. 3, Mar. 1992, pp. 613-617. (Spec, p. 5).
B. Liang et al., "Histological and mechanical investigation of the bone-bonding ability of anodically oxidized titanium in rabbits," Biomaterials 24 (2003), pp. 4959-4966.
J. T. Edwards, "Mechanical and morphologic investigation of the tensile strength of a bone-hydroxyapatite interface," Journal of Biomedical Materials Research, vol. 36, (1997), pp. 454-468.
H.-W. Kim et al., "Fluor-hydroxyapatite sol-gel coating on titanium substrate for hard tissue implants," Biomaterials 25 (2004), pp. 3351-3358.
P. A. Ramires et al., "The influence of titania/hydroxyapatite composite coatings on in vitro osteoblasts behaviour," Biomaterials 22 (2001), pp. 1467-1474.
E. J. Mackie, "Osteoblasts: novel roles in orchestration of skeletal architecture," The International Journal of Biochemistry & Cell Biology 35 (2003), pp. 1301-1305.
D.F. Williams, "The Williams Dictionary of Biomaterials," Liverpool, Liverpool University Press 1999.
D. F. Williams, "Biomaterials and tissue engineering in reconstructive surgery," Biomaterials (2003) Sādhanā vol. 28 2003 pp. 563-574.
D.F. Williams, "On the nature of biomaterials," Biomaterials 30 (2009) pp. 5897-5909.

* cited by examiner

*Primary Examiner* — Carol M Koslow
(74) *Attorney, Agent, or Firm* — Collard & Roe, P.C.

(57) ABSTRACT

Biocompatible wear resistant nanostructured thin film materials are provided for application as coatings in the fabrication of load-bearing implants, for example, orthopedic and dental prosthetics, dental crowns, implants for maxillofacial surgery, artificial limbs, fixtures etc. Requirements to these materials include high hardness, fatigue resistance, wear and corrosion resistance, biocompatibility and absence of toxicity. The multicomponent nanostructured coating (MNC) has high hardness, low elastic modulus, high adhesion to the substrate, low friction coefficient and wear rate, high resistance to long elastic strain to failure and plastic deformation, low surface roughness, negative surface charge in physiological media (4.5<pH<9), bioactive surface, biocompatibility and absence of toxicity. Biocompatible multicomponent nanostructured coatings for load-bearing implants are synthesized on the basis of titanium carbonitride with the addition of elements that improve the mechanical and frictional properties of the coating and provide for its bioactivity, biocompatibility and absence of toxicity. The overall concentrations of the main and additional elements in the coating are in the following relationship:

$$1, 2 < \frac{\sum X_i}{\sum Y_j} < 20,$$

where
$X_i$ is the overall concentration of the main elements (Ti, C, N) in the coating and $Y_j$ is the overall concentration of the additional elements (Ca, Zr, Si, K, Mn, O, P) in the coating. The elemental concentration in the coating is chosen to keep the following component ratios, at. %: Ti:30-50, C:15-40, N:0.5-30, O:5-25, Ca:0-7, Zr:0-20, Si:0-30, P:0-1.5, Mn:0-1.0, K:0-1.0.

1 Claim, No Drawings

BIOCOMPATIBLE MULTICOMPONENT NANOSTRUCTURED COATINGS FOR MEDICAL APPLICATIONS

CROSS REFERENCE TO RELATED APPLICATIONS

This application is the National Stage of PCT/RU2005/000529 filed on Oct. 28, 2005, which claims priority under 35 U.S.C. §119 of Russian Application No. 2005120397 filed on Jun. 30, 2005. The international application under PCT article 21(2) was published in English.

This invention relates to medical engineering, more particularly, to biocompatible wear resistant nanostructured thin film materials for application as coatings in the fabrication of load-bearing implants, for example, orthopedic and dental prosthetics, dental crowns, implants for maxillofacial surgery, artificial limbs, fixtures etc. Requirements to these materials include high hardness, fatigue strength, wear and corrosion resistance, bio-compatibility and absence of toxicity.

Known is a biocompatible coating for titanium and titanium alloy implants (RU 2154463, published 20 Aug. 2000) containing titanium oxide and calcium phosphate compounds (brought to overall oxide content) with the following component ratios, wt. %:
Titanium oxide:52-74
Calcium oxide:6-12
Phosphorus oxide:20-36

However, biologically active ceramics cannot be used as a coating on the surface of load-bearing implants due to their low fracture toughness.

Known is a biocompatible coating based on titanium nitride and sodium carbide (SU 1803096, published 23 Mar. 1993) with the following component ratios, wt. %:
Titanium nitride:20-50
Titanium silicide:2-5
Hydrated sodium carbide:25-30
Silicon oxides:balance This coating provides for a high adhesion of the plastic material with the metallic substrate in orthopedic dentistry, but its wear resistance is insufficient to provide for a long service life, and its osteoinductive properties are not adequate to the application.

The prototype of the invention disclosed herein is an amorphous coating containing hidroxyapatite and titanium (U.S. Pat. No. 6,344,276, published 5 Feb. 2002).

This coating has a high adhesion with substrate and a low coating material dissolution rate, but it does not posses the required combination of physical, mechanical, chemical and biological properties as are required for materials used for load-bearing implants.

The technical result achieved in this invention is providing a multicomponent nanostructured coating (MNC) having high hardness, low elastic modulus, high adhesion to the substrate, low friction coefficient and wear rate, high resistance to long elastic strain to failure and plastic deformation, low surface roughness, negative surface charge in physiological media (4.5<pH<9), biologically active surface, biocompatibility and absence of toxicity.

Said technical result is achieved as follows.

Biocompatible multicomponent nanostructured coatings for load-bearing implants are synthesized on the basis of titanium carbonitride with the addition of elements that improve the mechanical and frictional properties of the coating and provide for its bioactivity, biocompatibility and absence of toxicity. The overall concentrations of the main and additional elements in the coating are in the following relationship:

$$1,2 < \frac{\sum X_i}{\sum Y_j} < 20,$$

where
$X_i$ is the overall concentration of the main elements (Ti, C, N) in the coating and $Y_j$ is the overall concentration of the additional elements (Ca, Zr, Si, K, Mn, O, P) in the coating.

The elemental concentration in the coating is chosen to keep the following component ratios, at. %:
Ti:30-50
C:15-40
N:0.5-30
O:5-25
Ca:0-7
Zr:0-20
Si:0-30
P:0-1.5
Mn:0-1.0
K:0-1.0.

The required combination of the physical, mechanical, chemical, tribological and biological properties of the biocompatible MNCs is achieved by adding the above listed components in the appropriate concentrations to the coating composition.

Titanium carbonitride has a high hardness and high wear and corrosion resistances.

Coating deposition in an argon atmosphere produces a rough columnar structure having a high porosity. The addition of nitrogen to the coating composition leads to structural refinement and compaction and, in some cases, to complete suppression of the columnar structure. The grain size of such structures is usually within 20 nm. Film roughness reduces if nitrogen is added to the coating composition.

The optimum ratio of the metallic (Me) and nonmetallic (NMe) elements is Me/NMe=1.0-1.7, at which the coatings proved to have a NaCl type cubic structure.

The formation of the apatite layer is attributable to the formation of hydroxyl functional groups on the negatively charged surface of the bioactive ceramics in the inner body media. This is achieved by the addition of Ca, P and O in the amounts claimed herein. If the Ca, P and O concentrations exceed the amounts claimed herein, the mechanical and frictional properties of the coatings are impaired, their actine cytoskeleton is destroyed and their surface adhesion decreases (Table 1).

Over the entire pH range studied (4.5<pH<9), the MNC surface has a negative charge. Nitrogen containing coatings are usually more negatively charged. Thus, the surface of these coatings may attract positively charged $Ca^{2+}$ ions contained in the inner body media to favor the formation of first intermediate calcium containing phases and then an hydroxylapatite layer that is a stable phase in physiological media.

The addition of Ca, Zr and O significantly reduces the friction coefficient down to 0.17-0.25 as compared to titanium carbide (0.85) or titanium nitride (0.55) based coatings.

Cell attachment to the implant surface is controlled by the formation of integrin mediated focal contacts of cells with the underlying surface. Mn addition in amounts of up to 1 at. % activates the integrins and improves the cell adhesion. Further increase in the Mn concentration impairs the mechanical properties of the coatings and reduces cell spreading and multiplication. Silicon increases the activity of osteoblasts and favors the formation of the apatite layer. At Si concentrations of up to 30 at. % the coatings have a single phase NaCl type face centered cubic structure that is favorable for the mechanical and frictional properties of the coatings.

Composite targets and electrodes can be fabricated using the self-propagating high-temperature synthesis (SHS) method. Unlike other well-known composite refractory cathode synthesis methods (press sintering, gasostatic pressing, gas-thermal sputtering etc.), the SHS technology has valuable advantages, such as self-cleaning of the combustion products from noxious soluble and adsorbed impurities due to high process temperatures (2500-3000° C.) and combustion rates (2-10 cm/s) achieved in the combustion waves of SHS systems, high relative densities (97-99%) of the ceramic materials and refractory compounds at relatively low pressures, achievement of metastable states, i.e. supersaturated solid solutions, and obtaining of functional gradient materials (E. A. Levashov, A. S. Rogachev, V. I. Yukhivid and I. P. Borovinskays, Physicochemical and Technological Fundamentals of Self-Propagating High-Temperature Synthesis, Moscow, BIONOM, 1999, 174 pages).

Inorganic additions, such as hydroxylapatite ($Ca_{10}(PO_4)_6(OH)_2$), CaO, $ZrO_2$, $KMnO_4$ and $TiO_2$ etc.) can be introduced at the synthesis stage of composite target cathodes for ion-plasma and/or ion beam sputtering and spark deposition electrodes.

The main technological advantage of biocompatible MNC is the combination of numerous properties as are required for materials used for load-bearing implants:

high hardness H=15-35 GPa;
low elastic modulus E=150-300 GPa;
high coating adhesion strength which is characterized by the critical load $L_c$ at least 35 N;
low friction coefficient µ=0.1-0.25;
low wear rate $V_w$ less than $5 \cdot 10^6$ $mm^3/Nm$;
high resistance to long elastic strain to failure and plastic deformation; 0.1<H3/E2<0.9 GPa;
negative surface charge in physiological media;
no destruction of the actine cytoskeleton of the cells, combined with bioactive surface, biocompatibility and absence of toxicity.

Deviation of at least one of the above listed coating properties impairs the service parameters of the entire product (implant).

The low elastic modulus of the coatings is favorable because it provides for lower stresses between the coating and the implant, the later usually being stainless steel with E=190-200 GPa or titanium with E=116 GPa. The low Young modulus also improves the ability of the bones to withstand functional loads and favors the growth of bone tissues. The combination of high hardness and elastic recovery suggests the MNC as a new, unique and hard but still elastic material, these properties being of primary importance for medical applications where materials are to work under load.

The following embodiments of this invention are possible.

EXAMPLE 1

The technological route of the biologically compatible Ti—Zr—C—O—N MNC consists of two major stages: synthesis of the $TiC_{0.5}+ZrO_2$ composite target, e.g. with the self-propagating high-temperature synthesis (SHS) method, and its magnetron sputtering onto the substrate.

The Ti—Zr—C—O—N coating was deposited in an $Ar+N_2$ gas atmosphere. The coating composition was as follows, at. %:

C:18.0
O:7.9
N:27.6
Ti:44.5
Zr:2.0

For measurement of the physical, mechanical and frictional properties, the MNC were deposited onto VT 1-0 titanium alloy, Celit-N nickel alloy, Celit-C cobalt alloy and titanium nickelide substrates.

The physical, mechanical and frictional properties of the MNC were measured using the following high precision instruments: a Nano-hardness tester manufactured by CSM Instruments, Swiss; a Revetest scratch tester manufactured by CSM Instruments, Swiss; a Tribometer manufactured by CSM Instruments, Swiss; a scanning force microscope equipped with a sclerometric ultrahard fullerite $C_{60}$ needle hardness testing module NanoScan, Russia; an AXIOVERT optical microscope with a digital camera and an image analysis system manufactured by Karl Zeiss, Germany. The hardness and elastic modulus were measured using the Oliver and Pharr method [G. M. Pharr, W. C. Oliver, F. R. Brotzen. J. Mater. Res. 3, 613 (1992)] using a Berkovic indenter. The elastic recovery $W_e$ was calculated from the loading-unloading curves using the formula $W_e=(h_{max}-h_r)/h_{max}$, where $h_{max}$ is the maximum indenter penetration depth and $h_r$ is the residual indentation depth after unloading. The friction coefficient and the wear rate of the coatings were measured using a ball and disc friction tester under 1 N load at a linear speed of 10 cm/s. The tests were performed in physiological solution (100 ml $H_2O$+0.9 g NaCl). The counter part material was a 3 mm diameter ball of sintered $Al_2O_3$.

The coating has a hardness of 37 GPa, an elastic modulus of 270 GPa, an elastic recovery of 70%, a friction coefficient of 0.16 and a wear rate of $10^{-6}$ $mm^3/Nm$.

The actine cytoskeleton of cells was not found to be destroyed. Rat 1 fibroblasts and IAR-2 epitheliocytes were seeded onto the surface of films deposited onto glass substrates. The cells were incubated for 24, 48 and 72 h at 37° C. The glass substrates were exposed to 3.7% paraformaldehyde on a phosphate buffer layer for 10 min following which dyed with hematoxylin and exposed to a glycerin and phosphate buffered soline. The number of cells within the vision field was counted under a light microscope. The cells distributed and multiplied similarly well on the reference glass substrates and on the test coatings, which suggests that the coatings are adhesive and not toxic for the cells.

In vivo experiments were performed with mice. Teflon specimens with coatings were introduced under the skin of the animals. In 16 weeks the implants with capsules that grew around them were removed and tested for biocompatibility. The results showed the absence of inflammation reaction inside the capsules and tight contact of the cells to the coatings surface.

EXAMPLE 2

MNC were deposited by magnetron sputtering of a $TiC_{0.5}$+CaO composite SHS target in an argon atmosphere. The composite target contained 3.3 at. % nitrogen due to the intense interaction of titanium with nitrogen during an air combustion reaction. The coating composition was as follows, at. %:

C:30.2
O:22.9
N:3.3
Ti:38.2
Ca:5.4

The coating has a hardness of 31 GPa, an elastic modulus of 220 GPa, an elastic recovery of 70% and a friction coefficient of 0.17.

The actine cytoskeleton of cells was not found to be destroyed. In vitro and in vivo tests showed that the Ti—Ca—C—O—N coatings are biologically compatible, not toxic and do not cause inflammation reaction after implantation under the skin of mice. The fibroplast and epithelial cells multiplied well and had a good adhesion to the coating surface.

EXAMPLES 3-16

Numerous experiments with different target cathode compositions and magnetron sputtering of coatings were performed aiming at MNC composition optimization. Table 1 summarizes experimental results on the MNC and MNC properties that confirm the suitability of the MNC compositions claimed herein.

The MNC have one or more competitive advantages as are required for materials used in load-bearing implants: high hardness, low elastic modulus, high adhesion to the substrate, low friction coefficient and wear rate, high resistance to long elastic strain to failure and plastic deformation, low surface roughness, negative surface charge in physiological media (4.5<pH<9), bioactive surface, biocompatibility and absence of toxicity.

TABLE 1

Elemental Composition and Properties of Coating

| No | Ti | C | N | O | Ca | Zr | Si | Mn | K | P |
|---|---|---|---|---|---|---|---|---|---|---|
| Optimum Coatings Corresponding to the Claimed Composition ||||||||||| 
| 1 | 38.2 | 30.2 | 3.3 | 22.9 | 5.4 | — | — | — | — | — |
| 2 | 32.5 | 25.6 | 17.0 | 19.3 | 5.6 | — | — | — | — | — |
| 3 | 47.1 | 33.7 | 3.0 | 14.0 | — | 2.2 | — | — | — | — |
| 4 | 44.5 | 18.0 | 27.6 | 7.9 | — | 2.0 | — | — | — | — |
| 5 | 41.8 | 16.5 | 26.6 | 12.6 | 1.8 | — | — | — | — | 0.7 |
| 6 | 47.0 | 22.0 | 23.2 | 7.0 | 0.6 | — | — | — | — | 0.2 |
| 7 | 43.7 | 36.6 | — | 15.2 | 3.7 | — | — | 0.6 | 0.2 | — |
| 8 | 38.1 | 22.8 | 22.8 | 12.8 | 3.0 | | | 0.4 | 0.1 | |
| 9 | 34.1 | — | 22.8 | 16.0 | — | 2.1 | 25.0 | — | — | — |
| Non-Optimum Compositions Beyond the Ranges Claimed Herein ||||||||||| 
| 10 | 53.0 | 12.0 | 35.0 | — | — | — | — | — | — | — |
| 11 | 55.0 | 13.2 | 19.5 | 2.5 | 8.8 | — | — | — | — | — |
| 12 | 36.0 | 9.3 | 23.0 | 8.0 | — | 23.7 | — | — | — | — |
| 13 | 44.2 | 13.1 | 23.2 | 10.1 | 7.6 | — | — | — | — | 1.8 |
| 14 | 41.7 | 17.4 | 31.6 | 3.2 | 3.5 | — | — | 1.4 | 1.2 | — |
| 15 | 51.5 | — | 4.1 | 7.2 | — | 4.8 | 32.4 | — | — | — |
| 16 | 33.2 | 12.1 | 20.8 | 28.5 | 5.4 | — | — | — | — | — |

TABLE 1-continued

Elemental Composition and Properties of Coating

| No | H, GPa | E, GPa | $L_c$, N | $W_e$, % | μ | $V_w$, $10^{-6}$ mm$^3$/Nm | Cell actine cytoskeleton destruction |
|---|---|---|---|---|---|---|---|
| Optimum Coatings Corresponding to the Claimed Composition |||||||| 
| 1 | 31 | 220 | 40 | 70 | 0.17 | 1.0 | − |
| 2 | 16 | 160 | 42 | 53 | 0.21 | 1.2 | − |
| 3 | 28 | 270 | 50 | 58 | 0.16 | 1.0 | − |
| 4 | 37 | 270 | 46 | 70 | 0.16 | 0.9 | − |
| 5 | 27 | 240 | 40 | 66 | 0.21 | 4.0 | − |
| 6 | 22 | 230 | 44 | 61 | 0.24 | 4.8 | − |
| 7 | 16 | 180 | 38 | 57 | 0.2 | 4.2 | − |
| 8 | 15 | 160 | 39 | 56 | 0.2 | 3.8 | − |
| 9 | 26 | 250 | 45 | 60 | 0.4 | 4.0 | − |
| Non-Optimum Compositions Beyond the Ranges Claimed Herein |||||||| 
| 10 | 22 | 450 | 32 | 55 | 0.55 | 5.2 | + |
| 11 | 11 | 120 | 40 | 45 | 0.5 | 6.7 | + |
| 12 | 13 | 140 | 37 | 51 | 0.42 | 5.8 | − |
| 13 | 8 | 115 | 30 | 48 | 0.38 | 7.4 | + |
| 14 | 11 | 120 | 25 | 49 | 0.45 | 6.2 | + |
| 15 | 6 | 80 | 32 | 45 | 0.5 | 7.0 | + |
| 16 | 10.5 | 130 | 20 | 49 | 0.35 | 5.6 | + |

Here H is hardness, E is elastic modulus, $L_c$ is critical load, $W_e$ is elastic recovery, μ is friction coefficient and $V_w$ is wear rate

What is claimed is:

1. A biocompatible multicomponent nanostructured coating composition for load-bearing implants are synthesized on the basis of titanium carbonitride with the addition of necessary elements Ca, P, Mn, and K that improve the mechanical and frictional properties of the coating composition and provide for its bioactivity and absence of toxicity, wherein the overall concentrations of the main and additional elements in the coating composition are in the following relationship:

$$1.2 < \frac{\Sigma X_i}{\Sigma Y_j} < 20,$$

where $X_i$ is the overall concentration of the main elements (Ti, C, N) in the coating composition and $Y_j$ is the overall concentration of the additional elements (Ca, Zr, Si, K, Mn, O, P) in the coating composition, and wherein the elemental concentration in the coating composition is chosen to keep the following component ratios, at. %:
Ti:30-50
C:15-40
N:0.5-30
O:5-25
Ca:0.6-7
Zr:0-20
Si:0-30
P:0.2-1.5
Mn:0.4-1.0
K:0.1-1.0.

* * * * *

UNITED STATES PATENT AND TRADEMARK OFFICE
CERTIFICATE OF CORRECTION

| | | |
|---|---|---|
| PATENT NO. | : 8,075,682 B2 | Page 1 of 1 |
| APPLICATION NO. | : 12/085385 | |
| DATED | : December 13, 2011 | |
| INVENTOR(S) | : Evgeny Aleksandrovich Levashov et al. | |

It is certified that error appears in the above-identified patent and that said Letters Patent is hereby corrected as shown below:

On the title page, column 1, item [73], should read

-- Federal State Autonomous Educational Institution of Higher Professional Education "National University of Science and Technology "MISIS," Moscow (RU);

Evgeny Aleksandrovich LEVASHOV, Moscow (RU);

Dmitry Vladimirovich SHTANSKY, Moscow (RU);

Natalya Aleksandrovna GLOUSHANKOVA, Moscow (RU);

Igor Vladimirovich RESHETOV, Moscow (RU) --

Signed and Sealed this
Twenty-first Day of February, 2012

David J. Kappos
*Director of the United States Patent and Trademark Office*